(12) United States Patent
Popp et al.

(10) Patent No.: US 6,613,033 B1
(45) Date of Patent: Sep. 2, 2003

(54) PANT-LIKE ABSORBENT GARMENTS HAVING CURVED LEG CUFFS

(75) Inventors: Robert Lee Popp, Hortonville, WI (US); Joseph D. Coenen, Neenah, WI (US); Shawn A. Quereshi, Neenah, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/642,207

(22) Filed: Aug. 15, 2000

(51) Int. Cl.$^7$ ................................................. A61F 13/15
(52) U.S. Cl. ............................ 604/385.25; 604/385.28; 604/385.26
(58) Field of Search .................. 604/385.24, 385.25, 604/385.26, 385.27, 385.28, 396; 2/407, 400

(56) References Cited

U.S. PATENT DOCUMENTS

| | | | |
|---|---|---|---|
| 2,664,895 A | 1/1954 | Shulman | 128/287 |
| 3,338,992 A | 8/1967 | Kinney | 264/24 |
| 3,341,394 A | 9/1967 | Kinney | 161/72 |
| 3,371,668 A | 3/1968 | Johnson | 128/290 |
| 3,400,718 A | * 9/1968 | Saijo | 128/291 |
| 3,468,748 A | 9/1969 | Bassett | 161/122 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,061,063 A | 12/1977 | Brush | 83/55 |
| 4,100,324 A | 7/1978 | Anderson et al. | 428/288 |
| 4,300,562 A | 11/1981 | Pieniak | 128/287 |
| 4,300,967 A | 11/1981 | Sigl | 156/164 |
| 4,340,563 A | 7/1982 | Appel et al. | 264/518 |
| 4,371,417 A | 2/1983 | Frick et al. | 156/495 |
| 4,397,704 A | 8/1983 | Frick | 156/201 |
| 4,412,881 A | 11/1983 | Sigl | 156/164 |
| 4,432,823 A | 2/1984 | Moore | 156/164 |
| 4,486,192 A | 12/1984 | Sigl | 604/385 |
| 4,578,133 A | 3/1986 | Oshefsky et al. | 156/164 |
| 4,610,681 A | 9/1986 | Strohbeen et al. | 604/396 |
| 4,617,082 A | 10/1986 | Oshefsky et al. | 156/447 |
| 4,639,949 A | 2/1987 | Ales et al. | 2/400 |
| 4,640,726 A | 2/1987 | Sallee et al. | 156/85 |
| 4,641,381 A | 2/1987 | Heran et al. | 2/400 |

(List continued on next page.)

FOREIGN PATENT DOCUMENTS

| | | | | |
|---|---|---|---|---|
| CA | 1338133 | 3/1996 | | 117/26 |
| EP | 0 217 032 | 4/1987 | | D04H/13/00 |
| EP | 0 622 063 A2 | 11/1994 | | A61F/13/15 |
| EP | 0 998 893 A2 | 5/2000 | | A61F/13/472 |
| EP | 1 064 895 A2 | 1/2001 | | A61F/13/15 |
| EP | 1 106 154 A2 | 6/2001 | | A61F/13/494 |
| WO | WO 96/03949 | 2/1996 | | A61F/13/15 |
| WO | WO 96/14815 | 5/1996 | | A61F/13/15 |

*Primary Examiner*—Weilun Lo
*Assistant Examiner*—Jacqueline F Stephens
(74) *Attorney, Agent, or Firm*—Pauley Petersen Kinne & Erickson

(57) ABSTRACT

A pant-like absorbent garment having curved leg cuffs has a gasket-like fit. A chassis of the absorbent garment defines first and second leg openings with curved cut-outs in the chassis. A bonded portion is located between a first portion and a second portion of each of two elastic strands. The bonded portions are bonded to the first and second leg openings about a periphery of the curved cut-outs, thereby forming finished seams. Second portions of the elastic strands can form rolled edges. The resulting absorbent garment has a comfortable, gasket-like fit and an aesthetically pleasing, finished look about the leg openings.

40 Claims, 5 Drawing Sheets

U.S. PATENT DOCUMENTS

| | | | |
|---|---|---|---|
| 4,642,819 A | 2/1987 | Ales et al. | 2/400 |
| 4,646,362 A | 3/1987 | Heran et al. | 2/400 |
| 4,648,928 A | 3/1987 | Ales | 156/164 |
| 4,650,532 A | 3/1987 | Kloehn et al. | 156/204 |
| 4,663,220 A | 5/1987 | Wisneski et al. | 428/221 |
| 4,675,016 A | 6/1987 | Meuli et al. | 604/385 A |
| 4,687,477 A | 8/1987 | Suzuki et al. | 604/385 A |
| 4,726,873 A | 2/1988 | Ales et al. | 156/495 |
| 4,743,241 A | 5/1988 | Igaue et al. | 604/385 A |
| 4,747,846 A | 5/1988 | Boland et al. | 604/38 A |
| 4,786,346 A | 11/1988 | Ales et al. | 156/160 |
| 4,816,094 A | 3/1989 | Pomplun et al. | 156/85 |
| 4,863,542 A | 9/1989 | Oshefsky et al. | 156/160 |
| 4,883,549 A | 11/1989 | Frost et al. | 156/161 |
| 4,915,767 A | 4/1990 | Rajala et al. | 156/440 |
| 4,917,746 A | 4/1990 | Kons et al. | 156/164 |
| 4,940,464 A | 7/1990 | Van Gompel et al. | 604/396 |
| 4,943,340 A | 7/1990 | Ujimoto et al. | 156/496 |
| 4,946,539 A | 8/1990 | Ales et al. | 156/495 |
| 5,046,272 A | 9/1991 | Vogt et al. | 38/143 |
| 5,055,103 A | 10/1991 | Nomura et al. | 604/385.2 |
| 5,092,861 A | 3/1992 | Nomura et al. | 604/385.2 |
| 5,104,116 A | 4/1992 | Pohjola | 271/185 |
| 5,135,522 A | 8/1992 | Fahrenkrug et al. | 604/385.1 |
| 5,143,679 A | 9/1992 | Weber et al. | 264/288.8 |
| 5,147,487 A | 9/1992 | Nomura et al. | 156/164 |
| 5,156,793 A | 10/1992 | Buell et al. | 264/288.8 |
| 5,167,897 A | 12/1992 | Weber et al. | 264/288.8 |
| 5,171,388 A | 12/1992 | Hoffman et al. | 156/164 |
| 5,180,534 A | 1/1993 | Thomas et al. | 264/145 |
| 5,213,645 A | 5/1993 | Nomura et al. | 156/164 |
| 5,224,405 A | 7/1993 | Pohjola | 83/24 |
| 5,226,992 A | 7/1993 | Morman | 156/62.4 |
| 5,230,851 A | 7/1993 | Thomas | 264/145 |
| 5,259,902 A | 11/1993 | Muckenfuhs | 156/164 |
| 5,275,676 A | 1/1994 | Rooyakkers et al. | 156/164 |
| 5,318,741 A | 6/1994 | Thomas | 264/519 |
| 5,326,415 A | 7/1994 | Thomas et al. | 156/244.11 |
| 5,334,152 A | 8/1994 | Nomura et al. | 604/385.2 |
| 5,342,341 A | 8/1994 | Igaue et al. | 604/385.2 |
| 5,354,400 A | 10/1994 | Lavash et al. | 156/227 |
| 5,366,782 A | 11/1994 | Curro et al. | 428/137 |
| 5,385,706 A | 1/1995 | Thomas | 264/519 |
| 5,389,173 A | 2/1995 | Merkatoris et al. | 156/164 |
| 5,393,360 A | 2/1995 | Bridges et al. | 156/73.3 |
| 5,407,438 A * | 4/1995 | Hedlund et al. | 604/385.2 |
| 5,407,507 A | 4/1995 | Ball | 156/163 |
| 5,413,654 A | 5/1995 | Igaue et al. | 156/161 |
| D362,717 S * | 9/1995 | Caschette et al. | D24/126 |
| 5,454,803 A | 10/1995 | Sageser et al. | 604/385.2 |
| 5,500,075 A | 3/1996 | Herrmann | 156/494 |
| 5,503,919 A | 4/1996 | Litchholt et al. | 428/286 |
| 5,509,985 A | 4/1996 | Kock | 156/160 |
| 5,516,392 A | 5/1996 | Bridges et al. | 156/160 |
| 5,517,737 A | 5/1996 | Viltro et al. | 26/88 |
| 5,518,566 A | 5/1996 | Bridges et al. | 156/161 |
| 5,525,175 A | 6/1996 | Blenke et al. | 156/161 |
| 5,540,672 A | 7/1996 | Roessler et al. | 604/385.2 |
| 5,545,275 A * | 8/1996 | Herrin et al. | 156/731 |
| 5,547,531 A | 8/1996 | Allen et al. | 156/164 |
| 5,620,431 A * | 4/1997 | LeMahieu et al. | 604/385.2 |
| 5,622,578 A | 4/1997 | Thomas | 156/66 |
| 5,662,636 A | 9/1997 | Benjamin et al. | 604/385.2 |
| 5,704,930 A | 1/1998 | Lavash et al. | 604/385.2 |
| 5,723,087 A | 3/1998 | Chappell et al. | 264/284 |
| 5,733,401 A | 3/1998 | Linman et al. | 156/160 |
| 5,745,922 A | 5/1998 | Rajala et al. | 2/243.1 |
| 5,749,865 A | 5/1998 | Yamamoto et al. | 604/385.2 |
| 5,749,989 A | 5/1998 | Linman et al. | 156/160 |
| 5,772,825 A | 6/1998 | Schmitz | 156/164 |
| 5,776,121 A | 7/1998 | Roe et al. | 604/385.1 |
| 5,911,713 A | 6/1999 | Yamada et al. | 604/385.2 |
| 5,921,975 A | 7/1999 | Suzuki et al. | 604/385.2 |
| 6,423,047 B1 * | 7/2002 | Webster | 604/385.15 |

\* cited by examiner

PANT-LIKE ABSORBENT GARMENTS HAVING CURVED LEG CUFFS

FIELD OF THE INVENTION

This invention is directed to pant-like, personal care absorbent garments having aesthetically pleasing, yet fully functional, leg cuffs. The leg cuffs are curved, thereby producing a gasket effect.

BACKGROUND OF THE INVENTION

Pant-like absorbent garments, such as adult incontinence wear, as well as infant and children's diapers, swim wear and training pants, typically include a pair of leg openings having an elastic portion around each leg opening. The elastic portions are intended to fit snugly around a wearer's legs to prevent leakage from the garment.

Articles that incorporate conventional elasticized margins and conventional barrier flap configurations at their leg openings have, however, exhibited various shortcomings. For example, it has been difficult to avoid marking of the wearer's skin and difficult to maintain the desired gasketing of the leg openings when the articles are being worn. Even when the leg openings are fitted with an elastomeric material or otherwise elasticized, it has been difficult to maintain contact between the leg opening and the wearer's body for an effective containment of urine and feces. As a result, there has been a continued need for improved containment structures at the leg regions of the absorbent articles.

There is a need or desire for an absorbent garment having comfortable, gasket-like leg openings that are aesthetically pleasing, provide superior defense against leakage, and eliminate a need for separately attached leg elastics under a top layer of the garment.

SUMMARY OF THE INVENTION

The present invention is directed to a pant-like absorbent garment, such as a training pant, swimsuit, diaper, incontinence garment or similar absorbent vehicle, having curved leg cuffs resulting in comfortable, flexible, aesthetically pleasing leg openings. Furthermore, the resulting leg openings each has a protruding elastic portion that is form-fitting and provides a gasket. A contoured shape about the leg openings enhances the fit about a wearer's legs and eliminates a need for separately attached leg elastics under a top layer of the garment.

An elastic band that is either a composite elastic material or a ribbon of elastic can be applied to the leg opening area of a disposable pant to provide superior fit, aesthetics, and leakage performance around the entire leg area. This is accomplished by attaching the elastic ribbon with a thermal or adhesive line bond, or discrete bonds, around the entire leg opening. This bonded area is off-center on the elastic band and the elastic material is either stretched before application to provide tension in the elastic or the material becomes elasticized through an activation step. When the elastic band is allowed to gather from the bonded area it will naturally move in the direction of the leg opening. The elastic moves in this direction because it is the path of least resistance for the elastic to reach a relaxed state by gathering into the smallest circle possible.

The resulting product is an absorbent garment having comfortable, form-fitting leg openings with a finished look about the leg openings. This invention encompasses curved standing leg cuffs.

With the foregoing in mind, it is a feature and advantage of the invention to provide an absorbent garment with curved leg cuffs.

It is another feature and advantage of the invention to provide an absorbent garment having gasket-like leg openings.

It is a further feature and advantage of the invention to provide an absorbent garment having comfortable and aesthetically pleasing leg openings.

DEFINITIONS

Figure 1:
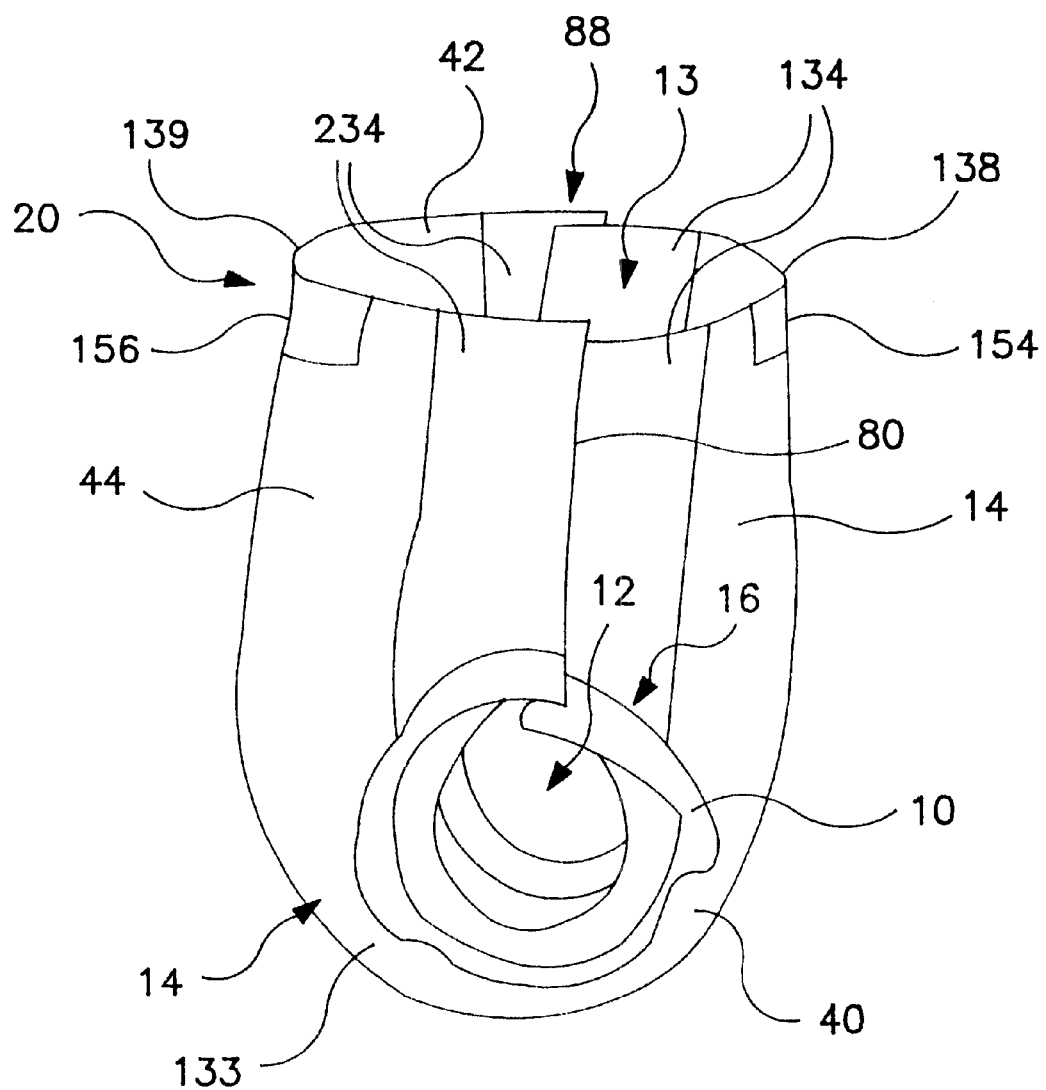
FIG. 1 is a side perspective view of an absorbent garment.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Curved" refers to an opening, band, flap, or edge, at least a portion of which is curved, i.e. has a radius of curvature and an arc covering at least 30°. Preferably, the opening, band, flap, or edge is curved over at least 90°, more preferably at least 180°.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Leg cuff" refers to leg elastics which are attached to a substrate along the length of the elastic material such that a portion of the material width is unattached and free to move relative to the substrate.

"Leg elastic" includes elastic bands, strands, films, ribbons, composites, filaments, filament bunches and the like, which are adjacent to a garment opening that receives a wearer's leg.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 8:
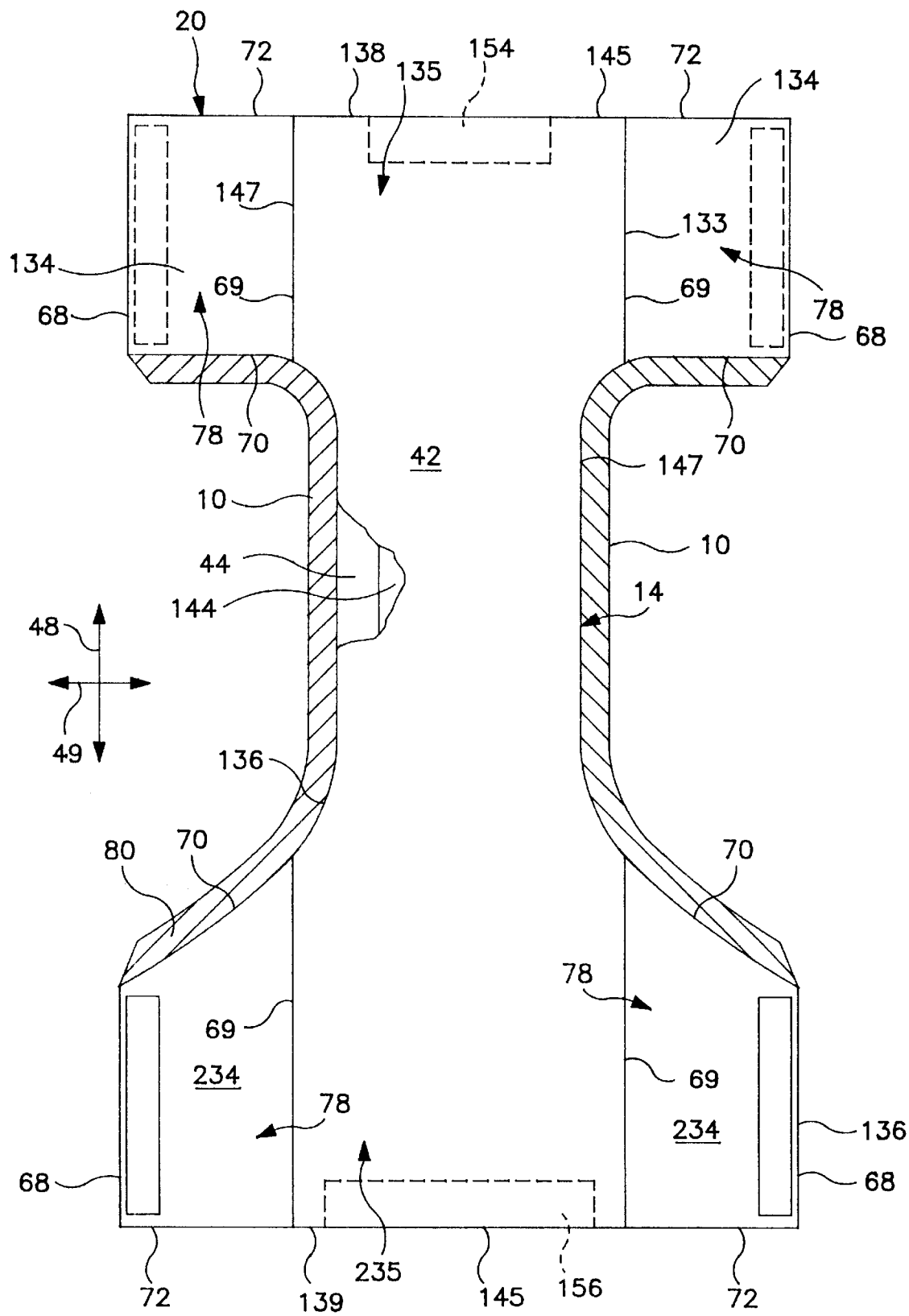
FIG. 8 is a plan view of the absorbent garment of FIG. 1 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 8. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Outward projecting portion" refers to a portion of a flap, a ribbon, a strand, or other member, that protrudes away from another portion of the member at an angle in a range of about 30–150°, more preferably in a range of about 60–120°.

"Peel force" and "peel strain" refer to forces that tend to pull two adjoining bodies away from one another in opposite directions generally perpendicular to a plane in which the bodies are joined.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

"Shearing strain" refers to forces that tend to produce an opposite but parallel sliding motion between two bodies' planes.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a pant-like absorbent garment having curved leg cuffs. Curved leg cuffs, in accordance with the invention, are leg elastics having an outward projecting elastic portion along the length of the leg cuffs and a bonded elastic portion also along the length of the leg cuffs. The outward projecting portion and the bonded portion are both part of a solitary unit of elastic. The bonded portion is a portion of the leg cuff that is bonded to a substrate. The unbonded portion may extend away from the bonded portion at an angle or lie juxtaposed to the bonded portion via a fold along the length of the leg cuff. The unbonded portion has greater freedom to respond to internal tension when the garment is in a relaxed state than the bonded portion, attributable to the fact that the bonded portion is bonded to the substrate in a stretched state, thereby causing the bonded portion to be restrained in movement by the substrate. The disproportionate freedom of movement along the length of the leg cuff causes a curvature of the leg cuff. In addition to the curvature caused by the disproportionate freedom of movement, the bonded portion is bonded to the substrate along a periphery of a curved cut-out in the substrate. The curved shape of the bonded portion increases the curvature of the leg cuffs.

The principles of the present invention can be incorporated into any suitable disposable absorbent article. Examples of such suitable articles include diapers, training pants, feminine hygiene products, incontinence products, other personal care or health care garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a disposable absorbent article, such as a training pant 20, is illustrated in a fastened condition. Leg cuffs 10 are used around leg openings 12 of the training pant 20 to reduce or prevent leakage. A main chassis 14 defines the leg openings 12 and a waist opening 13. When the leg cuffs 10 are curved, as in the present invention, the leg cuffs 10 are more form-fitting than straight edge leg elastics. The term "straight edge leg elastics" refers to typical leg elastics with no outward projecting portion that are wholly bonded along their entire length to a straight edge of a substrate. Furthermore, the curved leg cuffs 10 of the present invention create a gasket. The term "gasket" refers to a device that is used to block fluid leakage around the leg openings, between the garment and legs of a wearer. As a result, the leg openings 12 are gathered with low tension, since the leg openings 12 do not have to overcome forces from a main chassis 14 as straight edge leg elastics must overcome. The low tension and form-fit results in an absorbent garment 20 with increased comfort. Additionally, the curved leg cuffs 10 have a finished seam 16 where attached to the main chassis 14, resulting in an aesthetically pleasing appearance.

Figure 2:
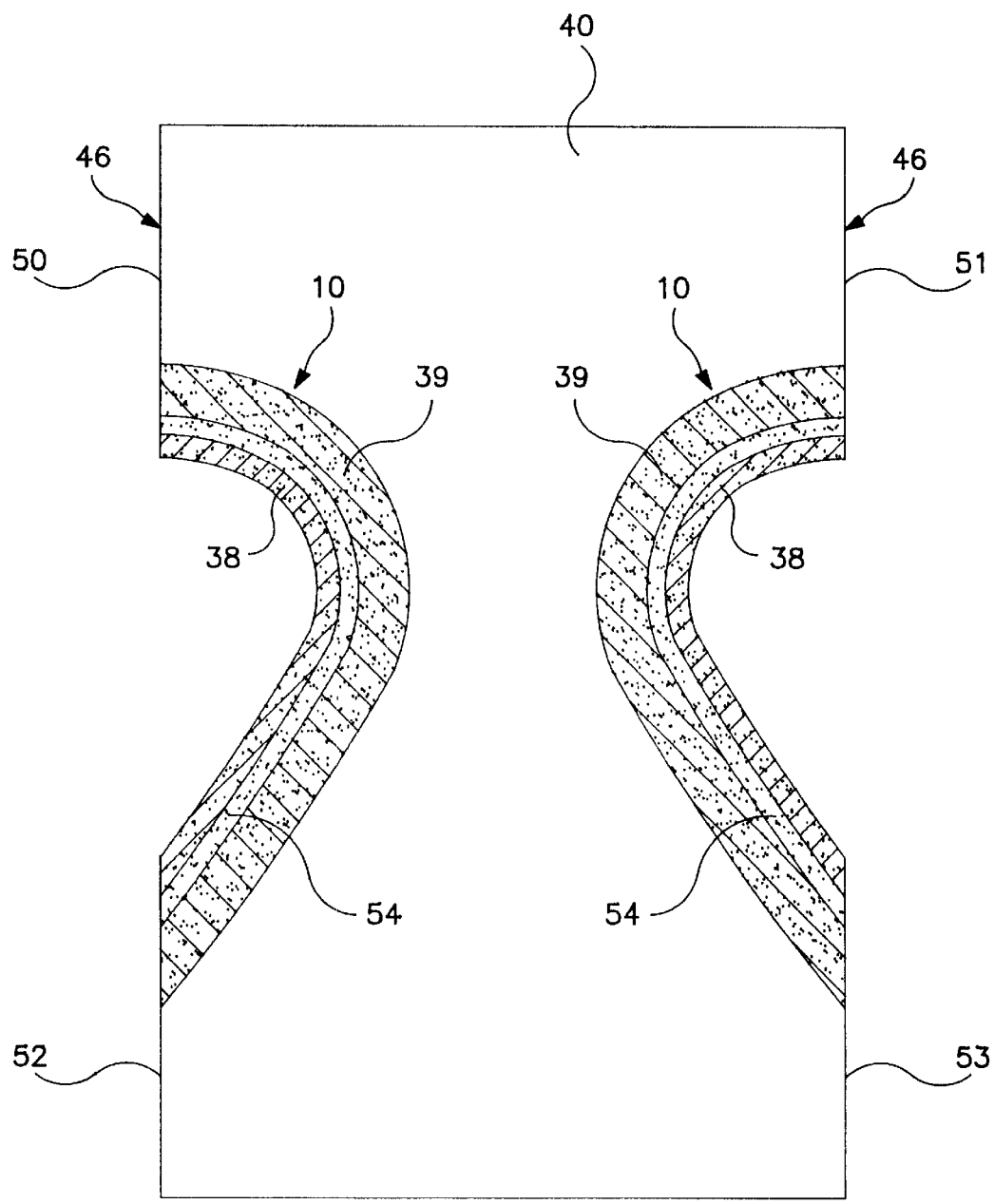
FIG. 2 is a plan view of a substrate, showing a pair of latent, curved leg cuffs bonded to the substrate.

The substrate 40, shown in FIG. 2, is typically a liner 42 or an outer cover 44 of the absorbent garment 20 (FIG. 1). As shown in FIG. 2, the substrate 40 preferably has a curved cut-out along at least one edge 46. The term "curved cut-out" refers to any cut-out having a curved edge, which may include a single material that is cut to form a cut-out or a plurality of materials that are bonded together to define a cut-out shape. A bonded area 54, wherein the leg cuff 10 is bonded to the substrate, is roughly parallel to the curved cut-out shape of the leg area. The parallel path of the bonded area 54 is toward the center of the product, putting the bonded area 54 at a larger radius as compared to the leg opening. The larger radius causes the leg cuff 10 to gather to the center of the leg opening during use as a pant, thereby allowing the leg cuff 10 to shrink to its most relaxed state in the product. Prior to the leg cuff 10 being bonded to the substrate 40, the curved cut-out is aligned with the bonded area 54 on the leg cuff 10 as shown in FIG. 2. As a result, a first portion 38 of the leg cuff 10 is bonded to the substrate 40 along an edge adjacent the curved cut-out. The substrate 40 is preferably stretchable, thereby providing great flexibility and allowing the leg cuffs 10 to be applied at low tension.

As a result, the first portions 38 of each of the leg cuffs 10 are bonded to the substrate 40 along an edge adjacent each of the curved cut-outs. A second portion 39 of each leg cuff 10 projects upward from the substrate 40 and serves as a gasket during later use of the garment 20, as explained below. The substrate 40 can be a continuous length, in which case the substrate 40 is cut into individual pieces for each garment 20 subsequent to the bonding process.

Figure 3:
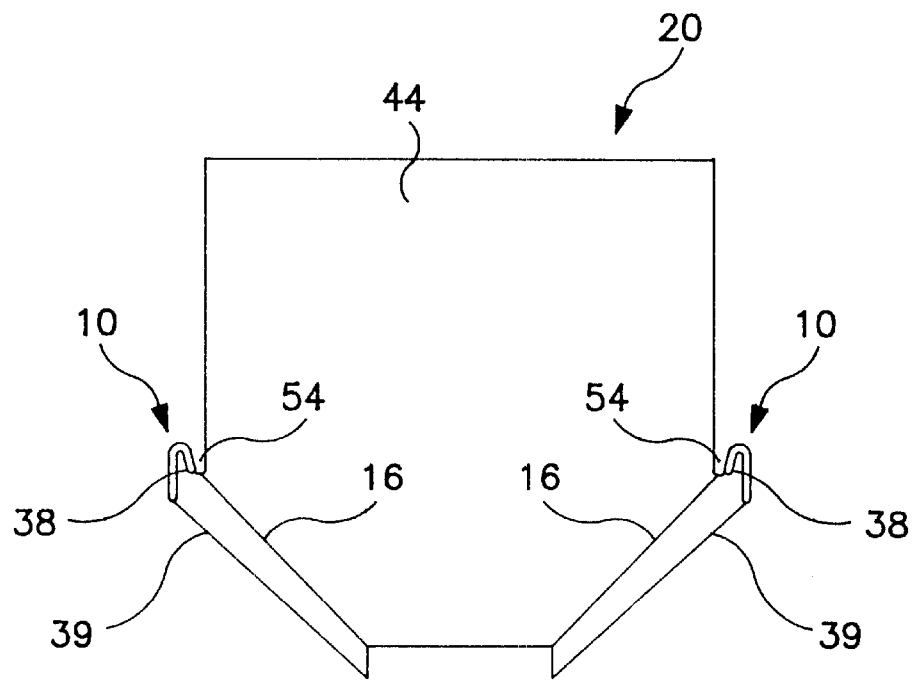
FIG. 3 is a front view of an absorbent garment showing how the leg cuffs are bonded to the substrate.

FIG. 3 is a front view of an absorbent garment 20 with a pair of curved leg cuffs 10 bonded to the substrate 40, in this case, the outer cover 44. Each of the curved leg cuffs 10 can be bonded to the substrate 40 either consecutively or simultaneously.

Figure 4:
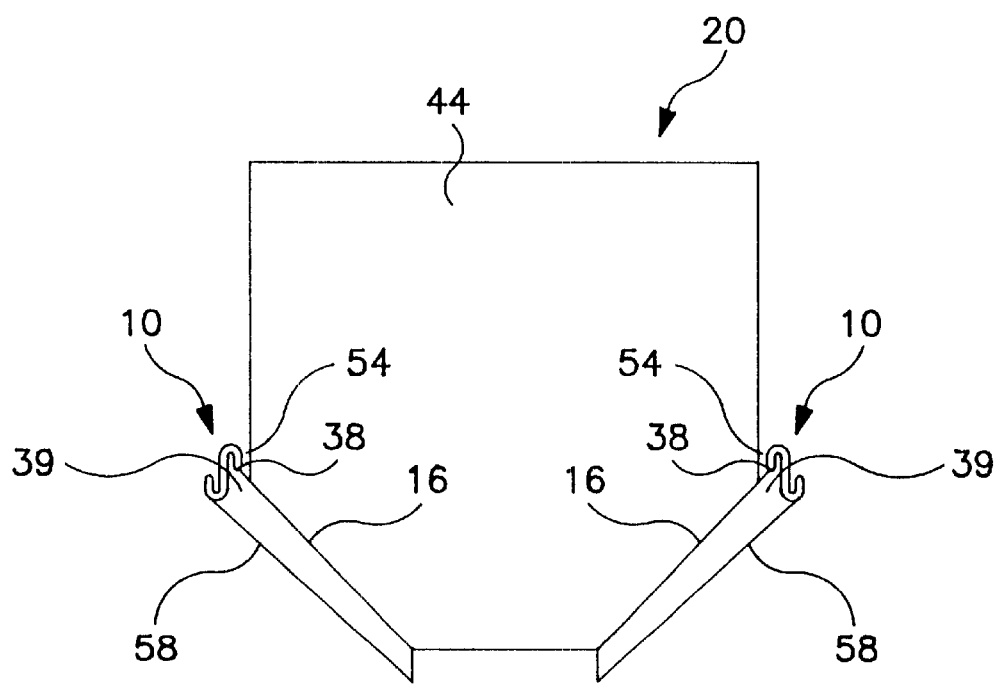
FIG. 4 is a front view of an absorbent garment showing leg cuff members with rolled edges.
Figure 5:
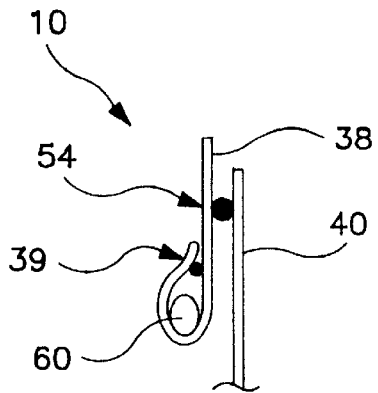
FIG. 5 is a cross-sectional view of an unactivated, applied leg cuff for use in a flat activation process.
Figure 6:
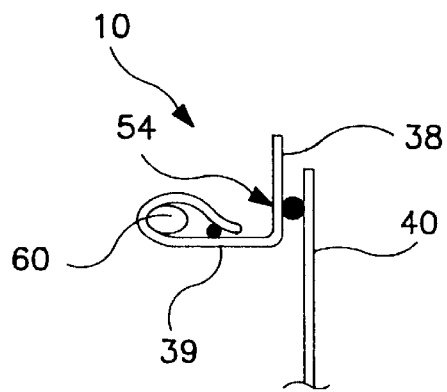
FIG. 6 is a cross-sectional view of an unactivated, applied leg cuff for use in a 90-degree application process.
Figure 7:
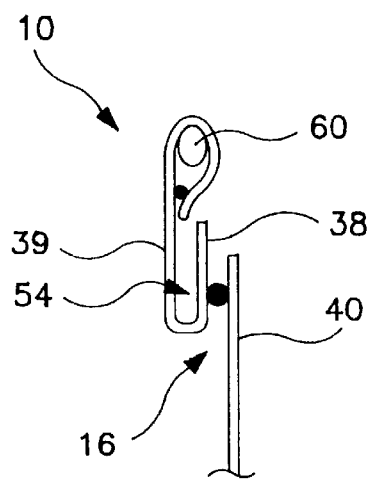
FIG. 7 is a cross-sectional view of an activated, applied leg cuff.

FIG. 4 is a front view of an absorbent garment 20 showing the curved leg cuffs 10 with rolled edges 58 forming a "J" shape. The rolled edges 58 provide greater strength and reinforcement around the leg opening 12, in addition to an even more finished look. FIGS. 5, 6 and 7 also show rolled edges 58. Rolled edges 58 have double the amount of elastic, thus double the tension and double the gasketing power, of non-rolled edges. An additional strand of elastic 60 can be located in the fold of the rolled edges 58, as shown in FIGS. 5, 6 and 7, to create even greater gathering of the leg cuff 10 to a smaller circumference to provide a better elastic gasket. The additional strand of elastic 60 is suitably an elastic-based material that is also heat activatable, as taught in U.S. Pat. No. 4,816,094 issued Mar. 28, 1989 to Pomplun, et al., incorporated herein by reference. The rolled edge 58 can be bonded by any suitable means, including adhesive bonding, ultrasonic bonding, thermal bonding, or mechanical bonding. A resulting seam 16, shown in FIG. 7, joining the leg cuffs 10 and the substrate 40 has a finished appearance since edges of the substrate 40 and the first portion of the leg cuffs 10 are both hidden from view on one side of the seam 16.

The first portions 38 of the leg cuffs 10 can be bonded to the substrate 40 by ultrasonic bonding, as mentioned, or a variety of other techniques including adhesive bonding, thermal bonding, stitch bonding or other conventional techniques. Suitable adhesives include spray adhesives, hot melt adhesives, self-adhering elastomeric materials and the like.

Once the leg cuffs 10 have been bonded to the substrate 40, edges 50 and 51 can be joined to edges 52 and 53, respectively, shown in FIG. 2, to form the garment 20 shown in FIG. 1. Once the garment 20 is formed, the second portions 39 of the leg cuffs 10 project from the garment surface. During use, the second portions 39 of the leg cuffs 10 firmly engage the wearer's skin, thereby serving as gaskets to reduce or prevent leakage through the openings of the garment 20.

Referring to FIG. 8, the absorbent garment 20 of FIG. 1 is shown in a partially disassembled, stretched flat state, showing a surface which faces the wearer when the garment is worn. In addition to defining the leg openings 12 and the waist opening 13 (FIG. 1), the absorbent chassis 14 also defines a pair of transversely opposed side edges 136 and a pair of longitudinally opposed waist edges, which are designated front waist edge 138 and back waist edge 139. The chassis 14 also includes a somewhat rectangular composite structure 133, a pair of transversely opposed front side panels 134, and a pair of transversely opposed back side panels 234. The composite structure 133 and side panels 134 and 234 may be integrally formed, as shown in FIG. 2, or may include two or more separate elements, as shown in FIGS. 1 and 8.

The illustrated composite structure 133 includes an outer cover 44, a body side liner 42 which is connected to the outer cover in a superposed relation, and an absorbent assembly 144 which is located between the outer cover 44 and the body side liner 42. The rectangular composite structure 133 has opposite linear end edges 145 that form portions of the front and back waist edges 138 and 139, and opposite linear, or curvilinear, side edges 147 that form portions of the side edges 136 of the absorbent chassis 14. Leg openings 12 (FIG. 1) are generally defined by portions of the transversely opposed side edges 136. For reference, arrows 48 and 49 depicting the orientation of the longitudinal axis and the transverse axis, respectively, of the training pant 20 are illustrated in FIG. 8.

The liquid permeable body side liner 42 is illustrated as overlying the outer cover 44 and absorbent assembly 144 (FIG. 8), and may but need not have the same dimensions as the outer cover 44. The body side liner 42 is desirably compliant, soft feeling, and non-irritating to the child's skin. Further, the body side liner 42 can be less hydrophilic than the absorbent assembly 144, to present a relatively dry surface to the wearer and permit liquid to readily penetrate through its thickness.

The absorbent assembly 144 (FIG. 8) is positioned between the outer cover 44 and the body side liner 42, which components can be joined together by any suitable means, such as adhesives, as is well known in the art. The absorbent assembly 144 can be any structure which is generally compressible, conformable, non-irritating to the child's skin, and capable of absorbing and retaining liquids and certain body wastes. The absorbent assembly 144 can be manufactured in a wide variety of sizes and shapes, and from a wide variety of liquid absorbent materials commonly used in the art. For example, the absorbent assembly 144 can suitably include a matrix of hydrophilic fibers, such as a web of cellulosic fluff, mixed with particles of a high-absorbency material commonly known as superabsorbent material. In a particular embodiment, the absorbent assembly 144 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 144 to better contain and absorb body exudates. The concentration of the superabsorbent particles can also vary through the thickness of the absorbent assembly 144. Alternatively, the absorbent assembly 144 can include a laminate of fibrous webs and superabsorbent material or other suitable means of maintaining a superabsorbent material in a localized area. Another type of absorbent material suitable for the absorbent assembly 144 is co-form, which is a blend of staple length and melt-blown fibers, as described in U.S. Pat. No. 4,100,324, incorporated herein by reference. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the co-form to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 144 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 144 in an amount of from about 0 to about 90 weight percent based on total weight of the absorbent assembly. The absorbent assembly 144 suitably has a density within the range of about 0.10 to about 0.35 grams per cubic centimeter. The absorbent assembly 144 may or may not be wrapped or encompassed by a suitable tissue wrap that maintains the integrity and/or shape of the absorbent assembly.

The absorbent chassis 14 can also incorporate other materials that are designed primarily to receive, temporarily store, and/or transport liquid along the mutually facing surface with the absorbent assembly 144, thereby maximizing the absorbent capacity of the absorbent assembly. One suitable material is referred to as a surge layer (not shown) and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Va., U.S.A.

A wide variety of elastic materials may be used for the leg cuffs 10. As is well known to those skilled in the art, suitable elastic materials include sheets, strands or ribbons of natural rubber, synthetic rubber, or thermoplastic elastomeric polymers, such as extruded polyurethane film. One particular type of suitable elastic material is stretch-bonded laminate (SBL), as described in greater detail below, with respect to elastic side panels.

The elastic materials can be stretched and adhered to a substrate, adhered to a gathered substrate, or adhered to a substrate and then elasticized or shrunk, for example with the application of heat; such that elastic constrictive forces are imparted to the substrate. One method of stretching elastic materials and adhering them to a substrate is taught in U.S. Pat. No. 4,883,549 issued Nov. 28, 1989 to Frost, et al., and is incorporated herein by reference. Heat shrinkable elastic is taught in U.S. Pat. No. 4,640,726 issued Feb. 3, 1987 to Sallee, et. al., and is incorporated herein by reference. In one particular embodiment, for example, the leg cuffs 10 include a plurality of dry-spun coalesced multifilament spandex elastomeric threads sold under the trade name LYCRA® and available from E.I. DuPont de Nemours and Company, Wilmington, Del., U.S.A., adhesively laminated between layers of nonwoven.

Each of the leg cuffs 10 preferably has a width of about 0.5 inch (1 cm) to about 5 inches (13 cm), more preferably about 1 inch (2.5 cm) to about 4 inches (10 cm), most preferably about 1.5 inches (4 cm) to about 2.5 inches (6 cm). Second portions 39 of the leg cuffs 10 preferably have a width of about 0.25 inch (0.6 cm) to about 4 inches (10 cm), more preferably about 0.5 inch (1 cm) to about 3 inches (7.5 cm), most preferably about 1 inch (2.5 cm) to about 2 inches (5 cm). The length of the leg cuffs 10 once cut by the cutting device 34 should substantially cover a circumference of the leg opening 12. Furthermore, each of the leg cuffs 10 preferably has elongation of 25–350%, more preferably about 30–260%, most preferably about 35–200%.

When the leg cuffs 10 are bonded to the outer cover 40, the width of the bonded area 54 is roughly between about 1 mm and about 25 mm, suitably between about 3 mm and about 12 mm, more suitable between about 4 mm and about 8 mm. Bonding can be carried out with either line bonds, discrete bonds, multiple line bonds, multiple rows of discrete bonds, or continuous pattern bonding such as adhesive swirl spray or meltblown spray. Continuous pattern bonding can include multiple continuous patterns having multiple orifices in the spray. Line bonds have a width in the above-stated bond width ranges and cover an entire length of the curved leg cuff 10. Discrete bonds are aligned in a row along the entire length of the curved leg cuff 10, each bond having a width in the above-stated bond width ranges. Discrete bonds are suitable because they put little resistance on the elastic band for gathering the elastic band where attached to the outer cover, in comparison to line bonds. Multiple line bonds include several lines of extruded adhesive that cover the entire length of the curved leg cuff 10. Multiple rows of discrete bonds include multiple rows of bonds that can be either offset from one another or parallel, and cover the length of the curved leg cuff 10. The bonds are desirably surface bonds to either the outer cover or the body side liner. Surface bonds simplify the process for attaching the leg cuffs 10. Furthermore, the bonds in the present invention are hidden from view because the leg cuff 10 automatically flips over the bond. The bonds are preferably moisture impervious to prevent leakage from occurring around the leg openings.

The bonded area 54 is suitably located off-center on the leg cuff 10, between the first portion 38 and the second portion 39, essentially dividing the leg cuff 10 between the first portion 38 and the second portion 39, as shown in FIG. 2. Not including the bonded area 54 of the leg cuff 10, the first portion 38 includes between about 0% and about 50% of the leg cuff 10 material and the second portion 39 includes between about 50% and about 100% of the leg cuff 10 material. For example, the first portion 38 can include approximately 25% of the leg cuff 10 material and the second portion 39 can include approximately 75% of the leg cuff 10 material not including the bonded area 54. Location of the bonded area 54 is important because both the first portion 38 and the second portion 39 work together to overcome resistance of the chassis material in the outer cover and body side liner in order to gather the leg opening to provide a gasket.

The design of this invention places great demands on the bond strength of the leg cuff 10 bond to the surface of the outer cover because the stress on the bond is in a peel strain, as opposed to a shearing strain. Shearing strain is the typical strain between elastic and an outer cover in order to insure that the elastic does not slip out of position due to the tension that is put on the bonds by both the elastic and the wearer.

When using heat activated, latent elastic in a flat application mode, the leg cuff 10 lies substantially flat on the web when applied, as shown in FIG. 5, until the activation process is applied to the leg cuff 10. FIG. 6 shows heat activated leg cuffs 10 prior to activation as applied with a 90 degree applicator. FIG. 7 shows the leg cuff 10 in a live state, or after heat activation. The leg cuffs 10 gather on the path of least resistance, which tends to create the smallest circumference possible. Thus both the first portion 38 and the second portion 39 gather towards the center of the leg opening. The bonded area 54 is restricted by the chassis and the chassis prevents the elastic bond area 54 from creating a smaller diameter. In comparison to non-latent elastic, latent leg cuffs 10 lend much ease to aligning edges 50 and 51 with edges 52 and 53, respectively, shown in FIG. 2.

The substrate 40 is preferably the outer cover 44 and desirably includes a material that is substantially liquid impermeable, and can be elastic, stretchable or nonstretchable. The outer cover 44 can be a single layer of liquid impermeable material, but desirably includes a multi-layered laminate structure in which at least one of the layers is liquid impermeable. For instance, the outer cover 44 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 44 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 44 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 44, is a 0.02 millimeter polyethylene film commercially available from Huntsman Packaging of Newport News, Va., U.S.A. If the outer cover 44 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 44. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 44 and bodyside liner 42 can include elastomeric materials, it can be desirable in some embodiments for the composite structure to be generally inelastic, where the outer cover, the bodyside liner and the absorbent assembly include materials that are generally not elastomeric.

As noted previously, the illustrated training pant 20 can have front and back side panels 134 and 234 disposed on each side of the absorbent chassis 14 (FIGS. 1 and 8). These transversely opposed front side panels 134 and transversely opposed back side panels 234 can be permanently bonded to the composite structure 133 of the absorbent chassis 14 and are releasably attached to one another by a fastening system 80. More particularly, as shown best in FIG. 8, the front side panels 134 can be permanently bonded to and extend transversely beyond the linear side edges 147 of the composite structure 133 along attachment lines 69, and the back side panels 234 can be permanently bonded to and extend transversely beyond the linear side edges of the composite structure along attachment lines 69. The side panels 134 and 234 may be attached using attachment means known to those skilled in the art such as adhesive, thermal or ultrasonic bonding. The side panels 134 and 234 can also be formed as a portion of a component of the composite structure 133, such as the outer cover 44 or the body side liner 42.

Each of the side panels 134 and 234 can include one or more individual, distinct pieces of material. In particular embodiments, for example, each side panel 134 and 234 can include first and second side panel portions that are joined at a seam, with at least one of the portions including an elastomeric material (See FIG. 8). Still alternatively, each individual side panel 134 and 234 can include a single piece of material which is folded over upon itself along an intermediate fold line (not shown).

The side panels 134 and 234 desirably include an elastic material capable of stretching in a direction generally parallel to the transverse axis 49 of the training pant 20. In particular embodiments, the front and back side panels 134 and 234 may each include an interior portion 78 disposed between a distal edge 68 and a respective front or back center panel 135 or 235. In the illustrated embodiment in FIG. 8, the interior portions 78 are disposed between the distal edges 68 and the side edges 147 of the rectangular composite structure 133. The elastic material of the side panels 134 and 234 can be disposed in the interior portions 78 to render the side panels elastomeric in a direction generally parallel to the transverse axis 49. Most desirably, each side panel 134 and 234 is elastomeric from a waist end edge 72 to a leg end edge 70. More specifically, individual samples of side panel material, taken between the waist end edge 72 and the leg end edge 70 parallel to the transverse axis 49 and having a length from the attachment line 69 to the distal edge 68 and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 44 or body side liner 42, or stretchable but inelastic materials.

The absorbent chassis 14 and the fastening system 80 together define a refastenable pant having a waist opening 13 and a pair of leg openings 12 (FIG. 1). When the fastening system is engaged, it can be appreciated that the refastenable pant includes a pair of elastomeric front side panels 134 extending from the waist opening to each leg opening, a pair of elastomeric back side panels 234 extending from the waist opening to each leg opening, a pair of refastenable seams 88 (FIG. 1) extending from the waist opening to each leg opening and positioned between the elastomeric front and back side panels, an elastomeric front waistband 154 positioned between the pair of elastomeric front side panels 134, an elastomeric back waistband 156 positioned between the pair of elastomeric back side panels 234, and a pair of curved leg cuffs 10 which encircle each leg opening 12. Alternatively, instead of refastenable seams 88, the absorbent garment of the invention can have bonded side seams.

As described herein, the various components of the training pant 20 can be integrally assembled together employing various types of suitable attachment means, such as adhesive, sonic and thermal bonds or combinations thereof. The resulting product is an absorbent garment 20 having a comfortable, gasket-like fit and an aesthetically pleasing, finished look about the leg openings 12. The pant-like absorbent garment 20 can be sized and tailored for a wide variety of uses including, for example, diapers, training pants, swimwear, adult incontinence garments, and the like. The curved leg cuffs 10 of the present invention can also be used for curved leak guard flaps.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A combination including a stretchable leg cuff and a substrate, the combination comprising:
   a stretchable leg cuff having a first longitudinal portion, a second longitudinal portion, and a bonded portion between the first longitudinal portion and the second longitudinal portion, wherein the bonded portion is bonded to the substrate around a perimeter of a curved cut-out in the substrate and the second longitudinal portion at least partially projects from the substrate; and a first longitudinal end segment of the first longitudinal portion of the leg cuff is joined to a second longitudinal end segment of the first longitudinal portion of the leg cuff, and a first longitudinal end segment of the second longitudinal portion of the leg cuff is joined to a second longitudinal end segment of the second longitudinal portion of the leg cuff, such that the leg cuff encircles a full perimeter of a leg opening.

2. The combination of claim 1 wherein the substrate comprises a stretchable material.

3. The combination of claim 1 wherein the substrate comprises an outer cover of an absorbent garment.

4. The combination of claim 1 wherein the substrate comprises a liner of an absorbent garment.

5. The combination of claim 1 wherein the second portion of the leg cuff comprises a rolled edge.

6. The combination of claim 1 wherein the leg cuff has a width in a range of about 1 centimeter to about 13 centimeters.

7. The combination of claim 1 wherein the leg cuff has a width in a range of about 2.5 centimeters to about 10 centimeters.

8. The combination of claim 1 wherein the leg cuff has a width in a range of about 4 centimeters to about 6 centimeters.

9. The combination of claim 1 wherein the second portion has a width in a range of about 0.6 centimeter to about 10 centimeters.

10. The combination of claim 1 wherein the second portion has a width in a range of about 1 centimeters to about 7.5 centimeters.

11. The combination of claim 1 wherein the second portion has a width in a range of about 2.5 centimeters to about 5 centimeters.

12. The combination of claim 1 wherein the bonded portion has a width in a range of about 1 millimeter to about 25 millimeters.

13. The combination of claim 1 wherein the bonded portion has a width in a range of about 3 millimeters to about 12 millimeters.

14. The combination of claim 1 wherein the bonded portion has a width in a range of about 4 millimeters to about 8 millimeters.

15. A diaper comprising the combination of claim 1.

16. Training pants comprising the combination of claim 1.

17. Swimwear comprising the combination of claim 1.

18. An incontinence product comprising the combination of claim 1.

19. An absorbent garment, comprising:
   a chassis defining a waist opening and first and second leg openings, wherein the first and second leg openings are defined by curved cut-outs in the chassis; and
   at least two stretchable curved leg cuffs, each curved leg cuff having a first longitudinal portion, a second longitudinal portion, and a bonded portion between the first longitudinal portion and the second longitudinal portion, wherein the bonded portion of each leg cuff is bonded to the chassis around a perimeter of one of the curved cut-outs and the second longitudinal portion of each leg cuff at least partially projects from the chassis, each leg cuff having a first longitudinal end segment of the first longitudinal portion joined to a second longitudinal end segment of the first longitudinal portion, and a first longitudinal end segment of the second longitudinal portion joined to a second longitudinal end segment of the second longitudinal portion, such that each curved leg cuff encircles a full perimeter of one of the first and second leg openings.

20. The absorbent garment of claim 19 wherein the chassis comprises a stretchable material.

21. The absorbent garment of claim 19 wherein the chassis comprises an outer cover layer and a liner layer.

22. The absorbent garment of claim 21 wherein the bonded portion of each of the curved leg cuffs is bonded to the outer cover layer.

23. The absorbent garment of claim 21 wherein the bonded portion of each of the curved leg cuffs is bonded to the liner layer.

24. The absorbent garment of claim 19 wherein the second portion of each of the curved leg cuffs comprises a rolled edge.

25. The absorbent garment of claim 19 wherein the first portion of each leg cuff comprises between about 0% and about 50% of a combination of the first portion and the second portion of each leg cuff.

26. The absorbent garment of claim 19 wherein the second portion of each leg cuff comprises between about 50% and about 100% of a combination of the first portion and the second portion of each leg cuff.

27. An absorbent garment, comprising:
   a chassis defining a waist opening and first and second leg openings, wherein the first and second leg openings are defined by curved cut-outs in the chassis;
   the chassis including at least a liquid-permeable body side liner, an absorbent layer and a substantially liquid-impermeable outer cover layer; and
   at least two stretchable curved leg cuffs, each curved leg cuff having a first longitudinal portion, a second longitudinal portion, and a bonded portion between the first longitudinal portion and the second longitudinal portion, wherein the bonded portion of each curved leg cuff is operatively attached in a stretched position to the chassis around a perimeter of one of the curved cut-outs and the second longitudinal portion of each leg cuff at least partially projects from the chassis, each curved leg cuff having a first longitudinal end segment of the first longitudinal portion joined to a second longitudinal end segment of the first longitudinal portion, and a first longitudinal end segment of the second longitudinal portion joined to a second longitudinal end segment of the second longitudinal portion, such that each curved leg cuff encircles a full perimeter of one of the first and second leg openings.

28. The absorbent garment of claim 27 wherein the bonded portion of each of the curved leg cuffs is bonded to the outer cover layer.

29. The absorbent garment of claim 27 wherein the outer cover layer comprises a stretchable material.

30. The absorbent garment of claim 27 wherein the bonded portion of each of the curved leg cuffs is bonded to the body side liner.

31. The absorbent garment of claim 30 wherein the body side liner comprises a stretchable material.

32. The absorbent garment of claim 27 wherein the second portion of each of the curved leg cuffs comprises a rolled edge.

33. The combination of claim 1, wherein at least part of the second portion overlays at least part of the bonded portion.

34. The absorbent garment of claim 19, wherein at least part of the second portion overlays at least part of the bonded portion.

35. The absorbent garment of claim 27, wherein at least part of the second portion overlays at least part of the bonded portion.

36. The combination of claim 1, wherein the second portion varies in width along the perimeter of the cut-out.

37. The absorbent garment of claim 19, wherein the second portion of each leg cuff varies in width along the perimeter of one of the cut-outs.

38. The absorbent garment of claim 27, wherein the second portion of each leg cuff varies in width along the perimeter of one of the cut-outs.

39. The combination of claim 1 wherein the first portion of the leg cuff comprises between about 0% and about 50% of a combination of the first portion and the second portion of the leg cuff.

40. The combination of claim 1 wherein the second portion of the leg cuff comprises between about 50% and about 100% of a combination of the first portion and the second portion of the leg cuff.

* * * * *